US012594163B2

(12) United States Patent (10) Patent No.: US 12,594,163 B2
Zhang et al. (45) Date of Patent: Apr. 7, 2026

(54) TISSUE GRIPPER AND VALVE CLAMPING DEVICE

(71) Applicant: HANGZHOU VALGEN MEDTECH CO., LTD., Hangzhou (CN)

(72) Inventors: Tingchao Zhang, Hangzhou (CN); Weiwei Zhang, Hangzhou (CN); Xianzhang Zheng, Hangzhou (CN); Yiwei He, Hangzhou (CN)

(73) Assignee: Hangzhou Valgen Medtech Co., Ltd., Hangzhou (CN)

( * ) Notice: Subject to any disclaimer, the term of this patent is extended or adjusted under 35 U.S.C. 154(b) by 558 days.

(21) Appl. No.: 18/112,513

(22) Filed: Feb. 22, 2023

(65) Prior Publication Data

US 2023/0200995 A1     Jun. 29, 2023

Related U.S. Application Data

(63) Continuation of application No. PCT/CN2021/085736, filed on Apr. 6, 2021.

(30) Foreign Application Priority Data

Aug. 21, 2020    (CN) .......................... 202010854973.7
Aug. 21, 2020    (CN) .......................... 202021775358.9

(51) Int. Cl.
*A61F 2/24* (2006.01)
(52) U.S. Cl.
CPC ...... *A61F 2/246* (2013.01); *A61F 2210/0014* (2013.01); *A61F 2220/0016* (2013.01);
(Continued)
(58) Field of Classification Search
CPC ............................... A61F 2/246; A61F 2/2454
See application file for complete search history.

(56) References Cited

U.S. PATENT DOCUMENTS

2017/0020521 A1* 1/2017 Krone .............. A61B 17/00234
2018/0325671 A1* 11/2018 Abunassar .............. A61F 2/246
(Continued)

FOREIGN PATENT DOCUMENTS

CN     103826548 A     5/2014
CN     107666868 A     2/2018
(Continued)

OTHER PUBLICATIONS

The extended European search report of the corresponding EP patent application No. 21857185.9, mail date Jan. 25, 2024.
ISR for PCT/CN2021/085736 mailed Jul. 2, 2021.

*Primary Examiner* — Rebecca S Preston
(74) *Attorney, Agent, or Firm* — The Sun IP Law

(57) ABSTRACT

A tissue gripper (60), includes a connecting frame (62) and two gripping arms (64). The connecting frame (62) includes two spaced connecting pieces (623), and the two gripping arms (64) are respectively arranged at sides of the two connecting pieces (623). Each gripping arm (64) includes a bending section (641) connected to the corresponding connecting piece (623) and a gripping section (643) connected to the bending section (641). The width of the bending section (641) is less than the width of the gripping section (643) and the width of the connecting piece (623), such that the weight of a valve clamping device (100) can be reduced, and the pulling force to pull the two gripping arms (64) up to a central axis can also be reduced. Also provided is the valve clamping device (100) provided with the tissue gripper (60).

12 Claims, 8 Drawing Sheets

(52) U.S. Cl.
CPC ................. *A61F 2220/0025* (2013.01); *A61F 2220/0091* (2013.01); *A61F 2250/0006* (2013.01); *A61F 2250/0036* (2013.01); *A61F 2250/0037* (2013.01); *A61F 2250/0069* (2013.01)

(56) References Cited

U.S. PATENT DOCUMENTS

| | | |
|---|---|---|
| 2019/0209298 A1 | 7/2019 | Metchik et al. |
| 2020/0163672 A1 | 5/2020 | Wei |

FOREIGN PATENT DOCUMENTS

| | | |
|---|---|---|
| CN | 107920813 A | 4/2018 |
| CN | 109717987 A | 5/2019 |
| CN | 111281607 A | 6/2020 |
| CN | 211243911 A | 8/2020 |
| CN | 111938869 A | 11/2020 |
| WO | 2018106482 A1 | 6/2018 |
| WO | 2020167677 A1 | 8/2020 |

* cited by examiner

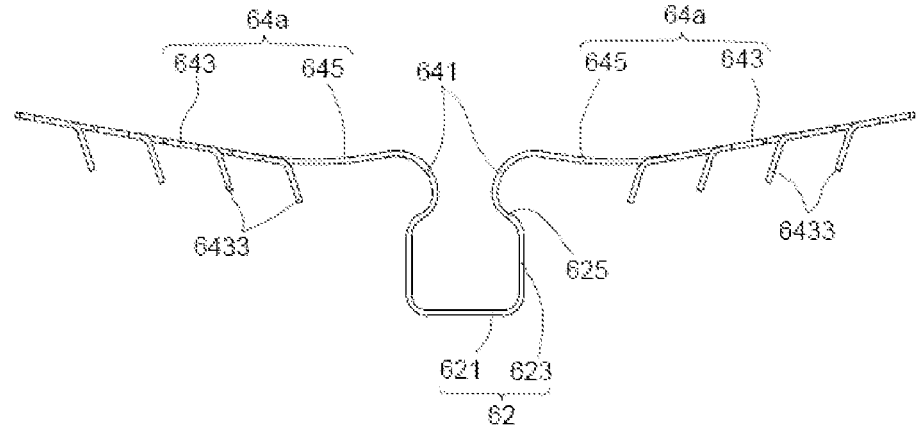

FIG. 15

| sample NO. | bending section structure | retraction force (Unit:N) | control line fatigue performance | barb fatigue performance |
|---|---|---|---|---|
| embodimentA1 | variable diameter with reduced width | 0.92 | pass | pass |
| embodimentA2 | variable diameter with reduced width | 0.94 | pass | pass |
| embodimentA3 | variable diameter with reduced width | 0.89 | pass | pass |
| embodimentA4 | variable diameter with reduced width | 0.95 | pass | pass |
| | | | | |
| comparativeB1 | constant diameter with equal width | 1.6 | failed | pass |
| comparativeB2 | constant diameter with equal width | 1.9 | failed | pass |
| comparativeB3 | constant diameter with equal width | 1.7 | failed | pass |
| comparativeB4 | constant diameter with equal width | 1.8 | failed | pass |
| | | | | |
| comparativeC1 | equal-width opening | 1.3 | pass | pass |
| comparativeC2 | equal-width opening | 1.3 | pass | failed |
| comparativeC3 | equal-width opening | 1.2 | pass | failed |
| comparativeC4 | equal-width opening | 1.3 | pass | pass |

FIG. 16

TISSUE GRIPPER AND VALVE CLAMPING DEVICE

TECHNICAL FIELD

The present application relates to the field of interventional medical devices, and in particular, to a tissue gripper and a valve clamping device.

BACKGROUND

Please refer to FIG. 1, the mitral valve 1 is a one-way valve located between the left atrium 2 and the left ventricle 3 of the heart. A normal healthy mitral valve 1 can control the blood flow from the left atrium 2 to the left ventricle 3, while preventing blood from flowing back into left atrium 2. The mitral valve 1 includes a pair of leaflets, referred to as an anterior leaflet 1a and a posterior leaflet 1b. The anterior leaflet 1a and the posterior leaflet 1b are connected to the papillary muscle of the left ventricle 3 through the chordae tendineae 4. Under normal circumstances, when the heart contracts, the edges of the anterior leaflet 1a and the posterior leaflet 1b are completely aligned, preventing blood from flowing back into the left atrium 2. Please refer to FIG. 2, when the leaflets of mitral valve 1 or their related structures change qualitatively or functionally, such as partial rupture of chordae tendineae 4, the anterior leaflet 1a and posterior leaflet 1b of mitral valve 1 are misaligned Therefore, when the heart contracts, the mitral valve 1 cannot be completely closed, resulting in the backflow of blood from the left ventricle 3 to the left atrium 2, thereby causing a series of pathophysiological changes, called "mitral regurgitation".

Surgical procedures such as edge-to-edge repair are usually used to treat mitral regurgitation. However, this type of surgical operation has disadvantages such as complicated operation process, high operation cost, severe trauma, high risk of complications, long hospital stay, and painful recovery process for patients. There is a minimally invasive treatment operation, which is based on the principle of edge-to-edge repair, that is a valve clamping device is delivered to the mitral valve through an interventional catheter, and then the anterior leaflet and the posterior leaflet of the mitral valve are clamped, so that the valve leaflets are drawn closer to each other, relieving "mitral regurgitation". The valve clamping device includes a pair of concave clamping arms and a tissue gripper made of shape memory material, and the valve leaflets of the mitral valve are clamped between the clamping arms and the tissue gripper. That is, the clamping arms and the tissue gripper capture the anterior leaflet and the posterior leaflet of the mitral valve at the same time, so as to achieve the purpose of fixing the valve leaflet and reducing mitral regurgitation.

Specifically, when the valve clamping device is in the delivery state, a tissue gripper is pulled by an elongate control line and then fitted to both sides of the central axis of the valve clamping device, and is delivered to the mitral valve through the elongate delivery catheter. Then the position of the valve clamping device is adjusted, and after the pulling of the control line on the tissue gripper is released, the tissue gripper expands due to its own shape memory property and presses the valve leaflet into the clamping arm, thereby cooperating with a clamping arm to hold the valve leaflets. Please refer to FIG. 3, the tissue gripper 3a includes a base 3a1 and gripping arms 3a2 disposed on opposite sides of the base 3a1. Each gripping arm 3a2 is provided with an opening 3a3 to reduce the stress at the position, reduce the pulling force, and increase the resilience; however, this gripping arm 3a2 reduces its own fatigue resistance; if the gripping arm 3a2 does not have an opening 3a3, to pull up the gripping arm 3a2 to fit the central axis of the valve clamping device requires a greater pulling force, and has higher requirements on the control line and the handle, which may easily lead to the breakage of the control line.

SUMMARY

In view of this, the present application provides a tissue gripper and a valve clamping device, which can not only improve the fatigue resistance of the tissue gripper, but also reduce the stress when the tissue gripper is in a folded state, so as to reduce the pulling force to pull the tissue gripper to the folded state, and thereby preventing the control line from breaking.

In order to solve the above technical problems, the present application provides a tissue gripper, which includes a connecting frame and two gripping arms, the connecting frame includes two connecting pieces spaced apart and opposite to each other; the two gripping arms are respectively arranged on sides of the two connecting pieces, each of the gripping arms extends to a side away from the other one of the gripping arms, and each gripping arm includes a bending section connected to the corresponding connecting piece, and a gripping section connected to the bending section and extending away from the corresponding connecting piece. A width of the bending section is less than the width of the gripping section, and less than the width of the connecting piece.

The present application also provides a valve clamping device, which includes a fixing base, a pair of clamping arms able to be open and close relative to the fixing base, and a tissue gripper. The tissue gripper is provided between the fixing base and the clamping arms, the two gripping arms of the tissue gripper are respectively cooperated with one of the pair of clamping arms to clamp the valve leaflets.

Each gripping arm of the valve clamping device provided by the present application has a bending section, and the width of the bending section is less than the width of the gripping section, and is less than the width of the connecting piece; thus not only can reduce the weight of the valve clamping device, but also being beneficial to the rebound of the gripping arm, reducing the difficulty of gripping, improving the fatigue resistance of the tissue gripper, and reducing the pulling force to pull the gripping arm up to fit the central axis through the control line, reducing the reverse force applied on the control line. This can prevent the breakage of the control line, improve the fatigue resistance of the valve clamping device implanted in the human body for a long time, and improve the safety and effectiveness of the device.

BRIEF DESCRIPTION OF THE ACCOMPANYING DRAWINGS

In order to illustrate the technical solutions of the embodiments of the present disclosure more clearly, the following briefly introduces the accompanying drawings that need to be used in the embodiments. As far as technical personnel are concerned, other drawings can also be obtained based on these drawings without any creative effort.

3

Figure 1:
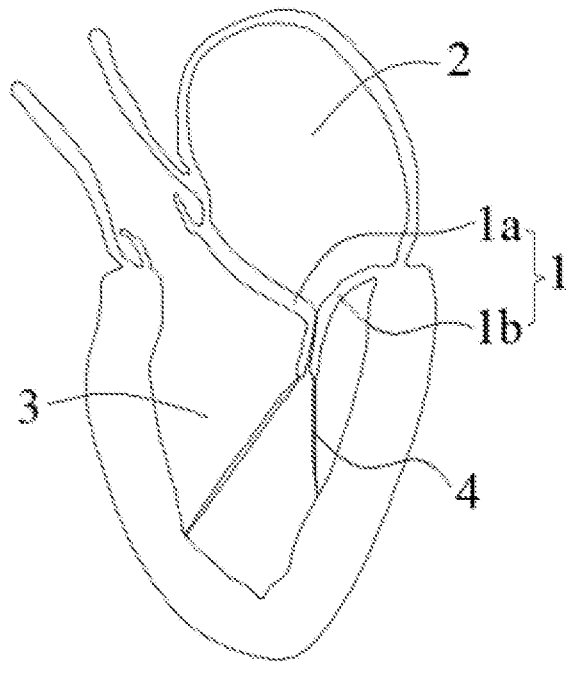
FIG. 1 is a schematic view of the mitral valve in a normal state.
Figure 2:
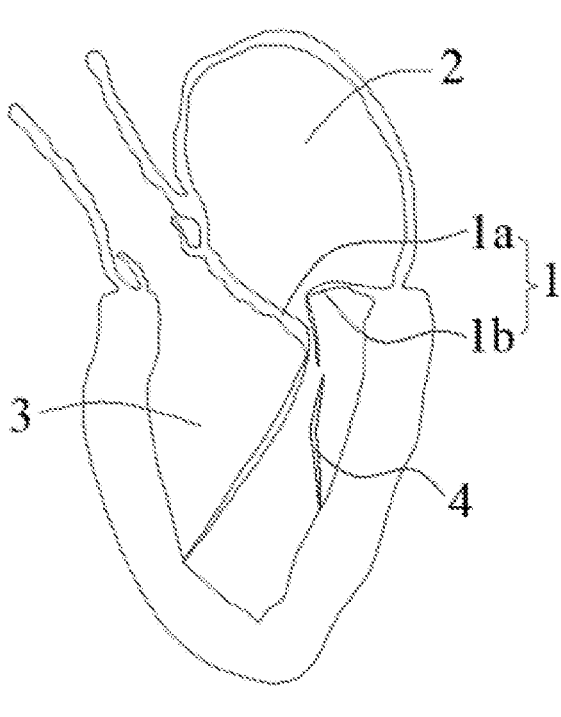
FIG. 2 is a schematic view of the mitral valve with lesions.
Figure 3:
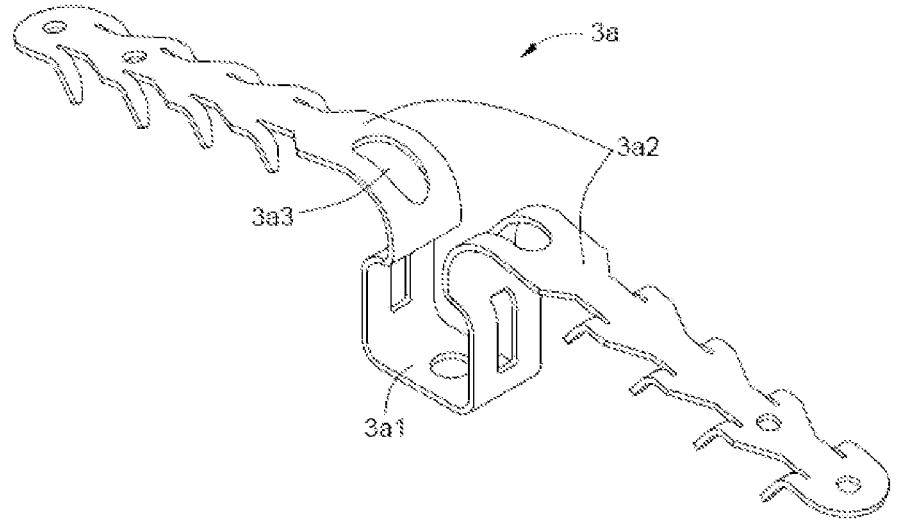

FIG. 3 is a schematic three-dimensional structural view of a tissue gripper in the prior art.

Figure 4:
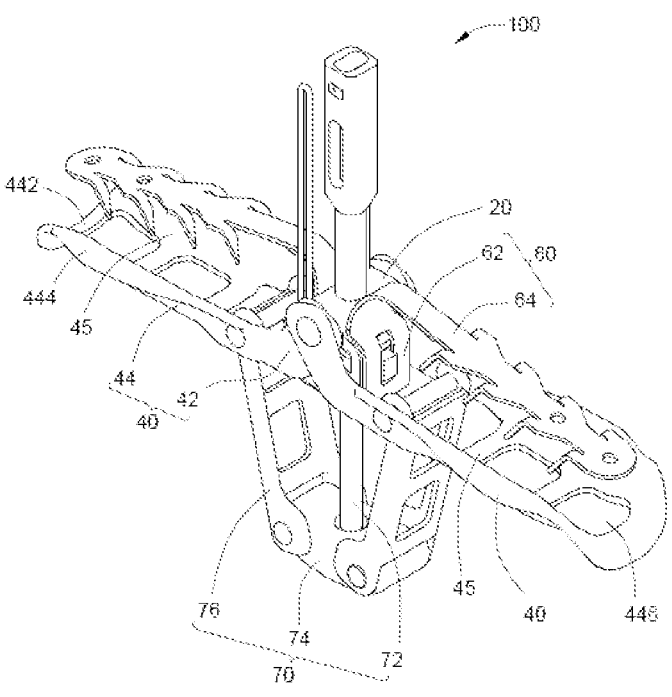

FIG. 4 is a schematic three-dimensional structural view of a valve clamping device provided in one embodiment of the present application.

Figure 5:
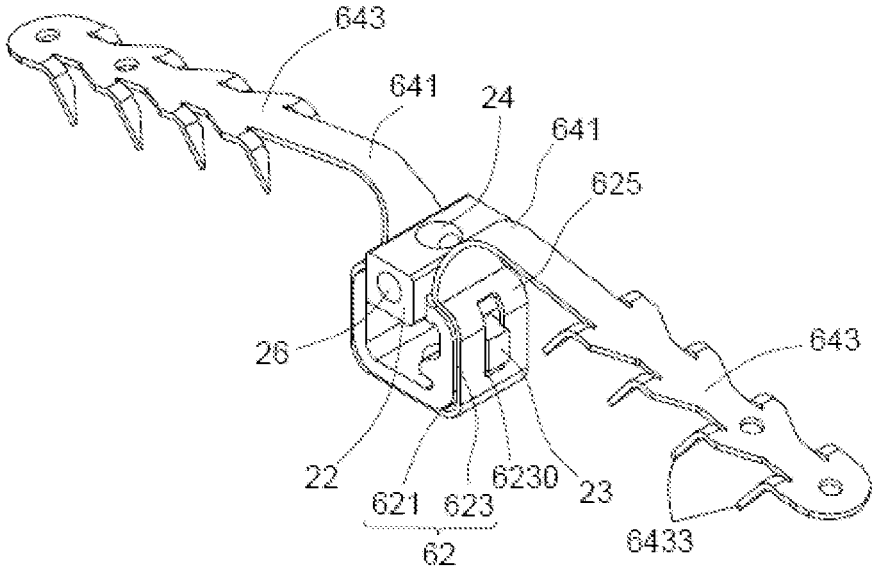

FIG. 5 is a schematic three-dimensional structural view of the tissue gripper and the fixing base of the valve clamping device in FIG. 4.

Figure 6:
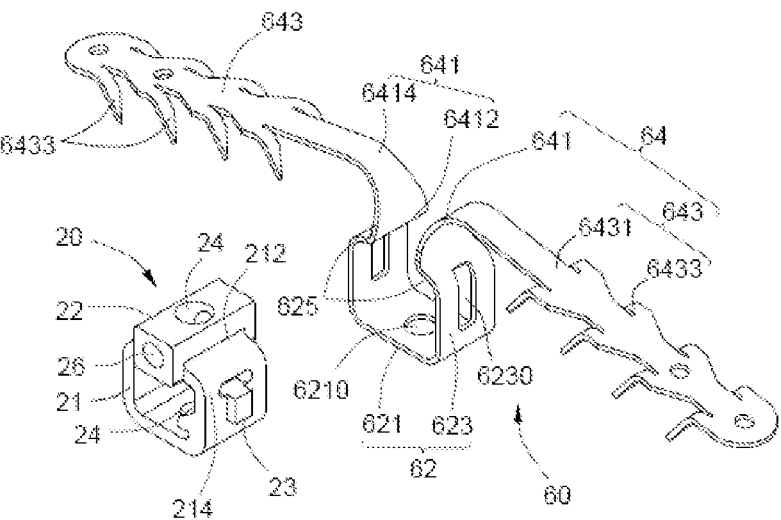

FIG. 6 is an exploded schematic view of the three-dimensional structural view of the tissue gripper and the fixing base in FIG. 5.

Figure 7:
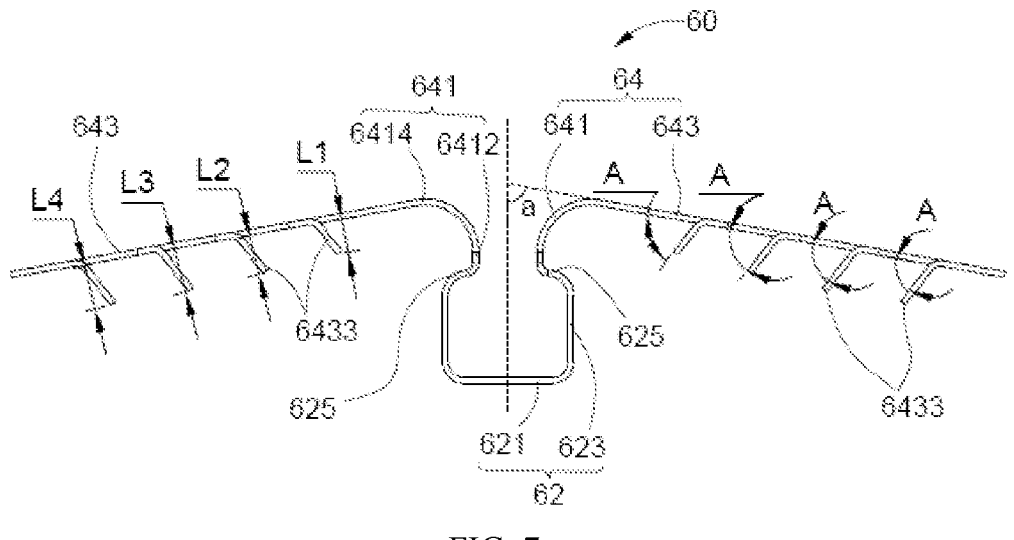

FIG. 7 is a side view of the tissue gripper of FIG. 6.

Figure 8:
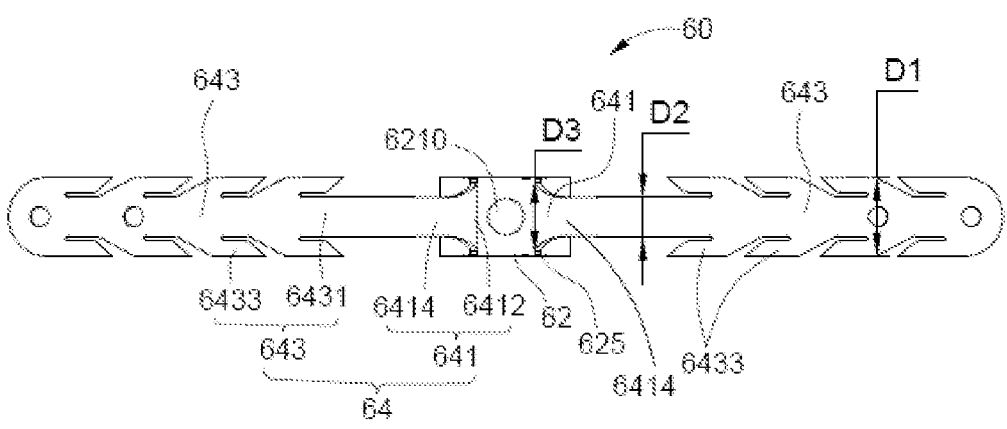

FIG. 8 is a top view of the tissue gripper of FIG. 6.

Figure 9:
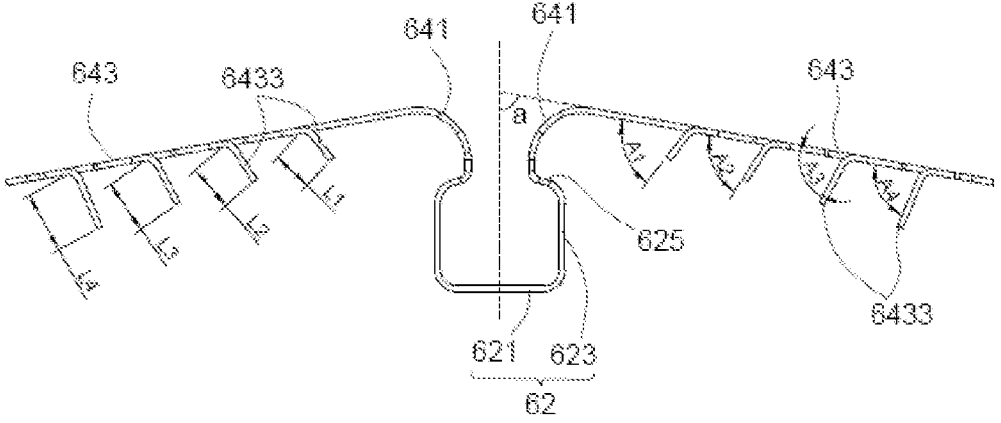

FIG. 9 is a schematic structural view of another embodiment of the tissue gripper in FIG. 7.

Figure 10:
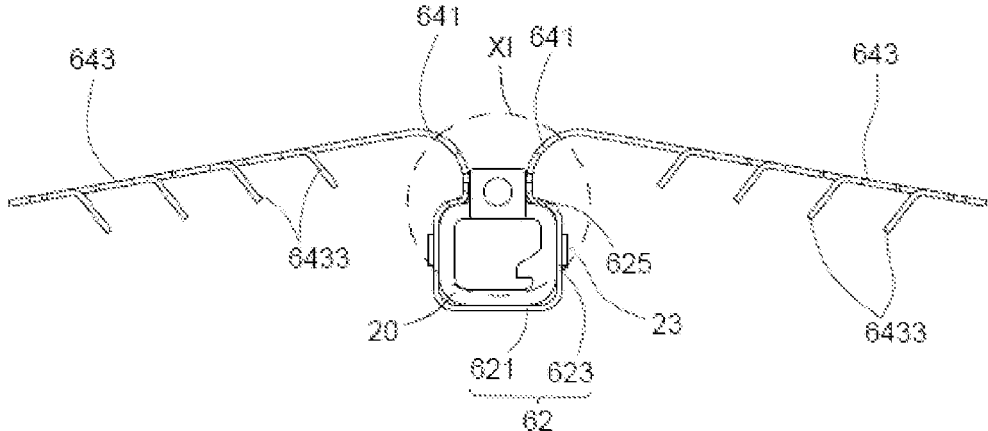

FIG. 10 is a side view of the tissue gripper and the fixing base of FIG. 5.

Figure 11:
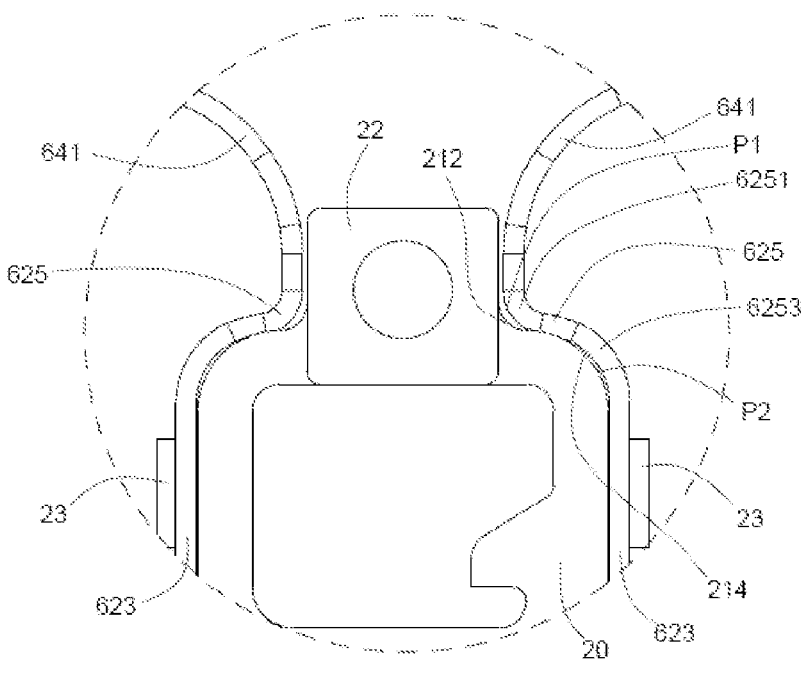

FIG. 11 is an enlarged view of part XI in FIG. 10.

Figure 12:
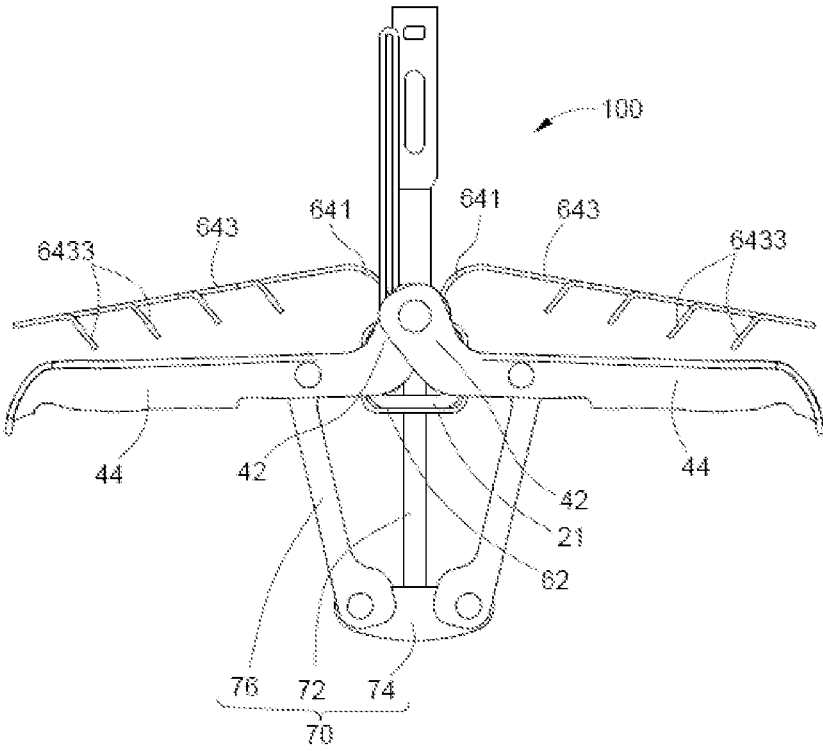

FIG. 12 is a side view of the valve clamping device of FIG. 4.

Figure 13:
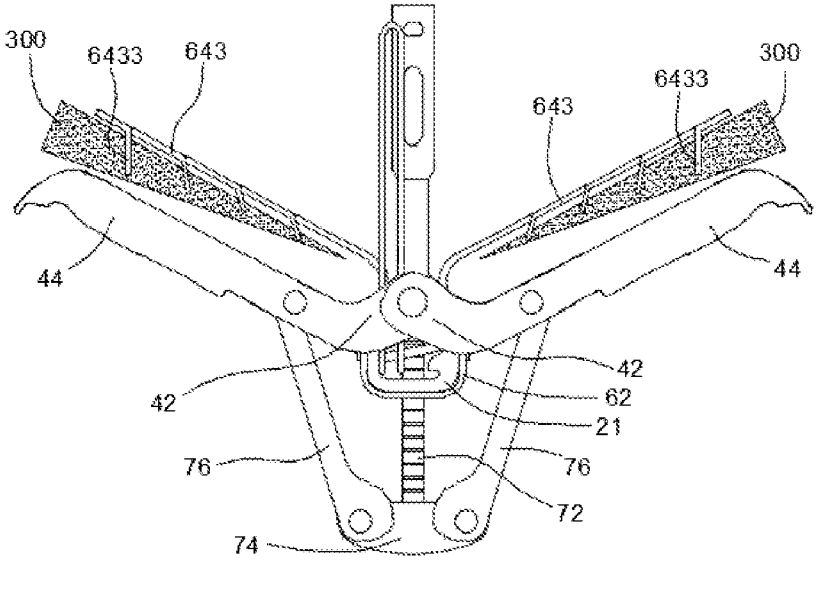

FIG. 13 is a use state of the valve clamping device in FIG. 4.

Figure 14:
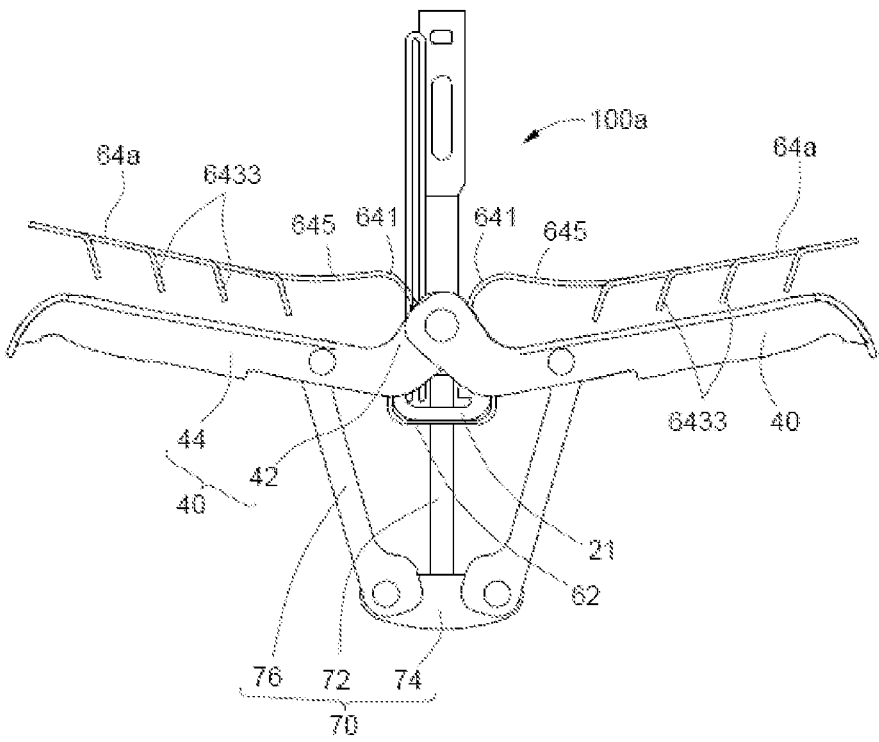

FIG. 14 is a schematic structural view of a valve clamping device provided by another embodiment of the present application.

FIG. 15 is a schematic structural view of the clamping arm of the valve clamping device in FIG. 14

FIG. 16 is a statistical chart of the results of the fatigue test and the performance test of the tissue gripper for the valve clamping device of the present application.

DETAILED DESCRIPTION OF ILLUSTRATED EMBODIMENTS

The technical solutions in the embodiments of the present application will be clearly and completely described below with reference to the drawings in the embodiments of the present application. Obviously, the described embodiments are only a part of the embodiments of the present application, but not all of the embodiments. Based on the embodiments in the present application, all other embodiments obtained by those of ordinary skill in the art without creative efforts fall within the protection scope of the present application.

In the description of the present application, it should be noted that the orientation or positional relationship indicated by the terms "upper", "lower", "inner", "outer", etc. is based on the orientation or positional relationship shown in the accompanying drawings, only for the purpose of It is for the convenience of describing the present application and simplifying the description, rather than indicating or implying that the referred device or element must have a particular orientation, be constructed and operate in a particular orientation, and therefore should not be construed as a limitation of the present application. Furthermore, the terms "first," "second," etc. are used for descriptive purposes only and should not be construed to indicate or imply relative importance.

In order to describe the structure of the tissue gripper and the valve clamping device more clearly, the defined terms "proximal end", "distal end" and "axial" described in this application are commonly used terms in the field of interventional medicine. Specifically, the "distal end" refers to the end that is far away from the operator during the surgical operation; the "proximal end" refers to the end that is close to the operator during the surgical operation; the proximal end in this application is relative to the distal distance from the operator (The distance from the surgeon) is relatively short, and after the device is assembled, each component in the device includes a proximal end and a distal end, wherein the proximal end of each component is closer to the operator than the distal end. "Axial" refers to the direction of the central axis of the device, and the radial direction is the direction perpendicular to the central axis. Unless otherwise defined, all technical and scientific terms used in this application have the same meaning as commonly understood by one of ordinary skill in the technical field to which this application belongs. The conventional terms used in the specification of the present application are only for the purpose of describing specific embodiments, and should not be construed as limitations of the present application.

It should be noted that when an element is referred to as being "fixed to" or "disposed on" another element, the element can be directly connected to the other element or indirectly connected to the other element through one or more connecting elements on a component. When an element is referred to as being "connected to" another element, it can be directly connected to the other element or connected to the other element through one or more connecting elements.

Please refer to FIG. 4 to FIG. 6 together. The first embodiment of the present application provides a valve clamping device 100, which includes a fixing base 20, at least a pair of clamping arms 40 hinged with the fixing base 20, a tissue gripper 60 connected to the fixing base 20, and an actuator assembly 70 for actuating the clamping arm 40 to open and close relative to the fixing base 20. In the present embodiment, a pair of clamping arms 40 can be open and close relative to the fixing base 20, and the tissue gripper 60 is provided between the fixing base 20 and the clamping arm 40, so as to cooperate with the clamping arm 40 to clamp the valve leaflet. The tissue gripper 60 includes a connecting frame 62 and two gripping arms 64. When in use, the proximal end of the valve clamping device 100 is releasably connected to a delivery device, and the two gripping arms 64 of the valve clamping device 100 are pulled up to the center axis of the valve clamping device 100 through the control line, and the valve clamping device 100 is deliveryed to the patient's mitral valve, and then the valve clamping device 100 is remotely operated, so that the clamping arm 40 is opened relative to the fixing base 20, and then the pulling force of the control line on the two gripping arms 64 is released, and the mitral valve is clamped. The anterior and posterior leaflets of the valve are respectively clamped by the clamping arms 40 and the corresponding gripping arms 64, so that the leaflets of the mitral valve are edge-to-edge coapted together, and then the connection between the delivery device and the valve clamping device 100 is released, the valve clamping device 100 remains in the patient as an implant in order to keep the coapted position of the valve leaflets together, achieve "edge-to-edge repair" of the mitral valve, reduce the patient's mitral valve regurgitation.

It should be noted that, the valve clamping device 100 and the delivery device can be delivered into the body of the patient by using a current guiding device such as an adjustable sheath, a preformed sheath, and the like.

Specifically, the connecting frame 62 includes a substrate 621 and two connecting pieces 623 arranged on opposite sides of the substrate 621. The two gripping arms 64 are arranged on sides of the respective two connecting pieces 623, and each of the gripping arms 64 extends away from the other one of the gripping arms 64. The gripping arm 64 includes a bending section 641 connected to the corresponding connecting piece 623 and a gripping section 643 connected to the bending section 641 away from the corresponding connecting piece 623. The width of the bending section 641 is less than the width of the gripping section 643 and less than the width of the connecting piece 623. Each of the two gripping arms 64 of the tissue gripper 60 cooperate with one of the pair of clamping arms 40 to clamp the valve leaflet 300 (shown in FIG. 13), that is, the gripping section 643 of each gripping arm 64 cooperates with one clamping arm 40 to clamp a valve leaflet 300.

In the present application, each gripping arm 64 of the valve clamping device 100 has a bending section 641, and the width of the bending section 641 is less than the width of the gripping section 643 and is less than the width of the connecting piece 623, therefore, not only reducing the weight of the valve clamping device 100, to be facilitated to the rebound of the gripping arm 64, reducing the difficulty of gripping, improving the fatigue resistance of the tissue gripper 60, and can also reduce the pulling force for pulling the gripping arm 64 up to the central axis of the valve clamping device 100 by the control line. The required pulling force can reduce the reverse force applied on the control line, prevent the control line from breaking, improve the fatigue resistance of the valve clamping device 100 implanted in the human body for a long time, and improve the safety and effectiveness of the device.

As shown in FIG. 4, in this embodiment, the valve clamping device 100 includes a pair of clamping arms 40 disposed opposite to each other, and each clamping arm 40 can be opened and closed relative to the fixing base 20. Each clamping arm 40 includes a connecting frame 42 and a clamping frame 44 connected to the end of the connecting frame 42 away from the fixing base 20. The ends of the connecting frames 42 of the two clamping arms 40 away from the clamping frame 44 are laminated to each other and hinged to the fixing base. 20. A leaflet accommodation space is formed between the gripping arm 64 and the clamping arm 40. The surface of each clamping arm 40 facing the gripping arm 64 is inwardly recessed to form a receiving groove 45, so that in the delivery state of the valve clamping device 100, the gripping arm 64 is at least partially accommodated in the receiving groove 45 of the clamping arm 40, thereby reducing the outer diameter and volume of the valve clamping device 100, thus it is convenient for delivery in the body. After the clamping arm 40 cooperates with the gripping arm 64 to clamp the valve leaflet 300, the valve leaflet 300 is clamped in the receiving groove 45, which can increase the contact area between the clamping arm 40 and the valve leaflet 300, and allow the gripping arm 64 press the valve leaflet 300 into the receiving groove 45 of the clamping arm 40 to increase the clamping force on the valve leaflet 300.

Specifically, each clamping arm 40 includes a rectangular connecting plate 442 and side plates 444 disposed on opposite sides of the connecting plate 442, the connecting plate 442 and the two side plates 444 enclose a receiving groove 45. The connecting plate 442 defines a number of through holes 446 along its length for removing material to reduce the weight of the clamping arm 40. One end of the side plate 444 adjacent to the fixing base 20 extends obliquely and is hinged on the fixing base 20 to form the connecting portion 42 of the clamping arm 40, and the connecting portion 42 defines a pin hole for inserting a pin.

The clamping arm 40 is opened and closed relative to the fixing base 20 through the actuator assembly 70. The actuator assembly 70 includes an actuator shaft 72 passing through the fixing base 20, a connecting base 74 disposed at a distal end of the actuator shaft 72, and a pair of connecting rods 76 movably connected to two sides of the connecting base 74. One end of each connecting rod 76 is connected to a corresponding clamping arm 40, and the other end of the connecting rod 76 is pivotally connected to the connecting base 74, that is, each clamping arm 40 is connected to the distal end of the connecting base 74 of the actuator assembly 70 through the connecting rod 76 at the corresponding side. The actuator shaft 72 movably passes through the fixing base 20 and is connected to the connecting base 74. When the actuator shaft 72 slides axially relative to the fixing base 20, the connecting base 74 moves axially to rotate the connecting rod 76 and actuate the clamping arm 40 to open and close relative to the fixing base 20.

As shown in FIG. 6, the fixing base 20 includes a rectangular fixing frame 21, a connecting block 22 arranged at the proximal end of the fixing frame 21, and protrusions 23 arranged on opposite sides of the fixing frame 21. There is a through hole 24 penetrating through the connecting block 22 and the fixing frame 21, and the through hole 24 is used for passing the actuator shaft 72. The opposite ends of the connection block 22 are respectively provided with pin holes 26, the axes of the pin holes 26 and the through holes 24 are perpendicular to each other, and the pin holes 26 are used to connect with the connecting portion 42 of the clamping arm 40 through pins. The fixing frame 21 is respectively provided with a first curved fitting surface 212 and a second curved fitting surface 214 on opposite sides of the connecting block 22, wherein the first curved fitting surface 212 is closer to the connecting block 22 than the second curved fitting surface 214, and the curvature radius of the first curved fitting surface 212 is K1, and the curvature radius of the second curved fitting surface 214 is K2.

The tissue gripper 60 is at least partially made of shape memory material, and after heat setting treatment, the tissue gripper 60 has a natural unfolded state and a folded state. During production, the shape memory material is first cut into the required shape by laser cutting, and then placed in a mold and heat-set at about 550° C. to make it have a specific shape. As shown in FIG. 7, in a natural state, the gripping arms 64 on both sides of the tissue gripper 60 extend radially outward relative to the connecting frame 62; preferably, the gripping arms 64 extend obliquely toward the distal end so as to facilitate to cooperate with the clamping arms 40 to clamp the leaflet, that is, the angle between the gripping arms 64 on both sides in the naturally unfolded state should be slightly greater than the angle between the two clamping arms 40 to provide more stable clamping force, so as to ensure that there is a certain clamping force between the gripping arm 64 and the clamping arm 40, so as to clamp the valve leaflet. Specifically, the included angle a between the length direction of the gripping section 643 of each gripping arm 64 and the axial direction of the fixing base 20, is greater than the angle between the corresponding clamping arm 40 and the axial direction of the fixing base 20 when the clamping arm 40 corresponding to the gripping arm 64 is fully opened relative to the fixing base 20, so that the free end of each gripping arm 64 is close to the corresponding clamping arm 40 and has a certain clamping force, so as to provide a more stable clamping force. Specifically, in the natural state, the angle a between the length direction of the gripping section 643 and the axial direction of the fixing base 20 ranges from 0 to 150 degrees, that is, the angle between the two gripping sections 643 can reach 300 degrees at most, preferably 160-200 degrees. In this embodiment, the angle between the two gripping sections 643 is greater than 180 degrees.

In present embodiment, the tissue gripper 60 as a whole is made of super-elastic nickel-titanium alloy, so as to provide elastic force for the tissue gripper 60 to drive the gripping arm 64 closer to the clamping arm 40 to clamp the leaflet, and reduce production process difficulty, simplify process flow, reduce production cost.

In other embodiments, different parts of the gripping arm 64 can be separately made of different materials and fixedly connected. For example, the gripping section 643 of the gripping arm 64 is made of stainless steel to improve the gripping force, and the bending section 641 should have a bending function so as to provide the tissue gripper 60 with a natural unfolded state and a folded state that is conducive to transportation, therefore the bending section 641 is made of shape memory material.

In present embodiment, each connecting piece 623 is connected to the corresponding bending section 641 through a bent fixing piece 625, and the fixing piece 625 on each connecting piece 623 bends toward the other connecting piece 625, and each bending section 641 bends away from the other bending section 641. Each connecting piece 623 is provided with a slot 6230 along its length, and the slot 6230 extends into the corresponding fixing piece 625 for cooperating and fixing with the fixing base 20. The shape of the slot 6230 can be rectangular, elliptical, prismatic or other shapes. In present embodiment, the rectangular shape is preferred, and the matching stability is higher. The substrate 621, two connecting pieces 623 and two fixing pieces 625 enclose a connecting frame 62 with an open proximal end, the fixing base 20 is accommodated in the inner cavity of the connecting frame 62, and the actuator shaft 72 is inserted in the fixing base 20 and the connection frame 62 through the opening of the proximal end of the connecting frame 62. Specifically, the substrate 621 is provided with a through hole 6210, the fixing base 20 is accommodated in the inner cavity of the connection frame 62, the through hole 24 of the fixing base 20 aligns with the through hole 6210 of the substrate 621, and the actuator shaft 72 is passed through the through hole 24 of the fixing base 20 and the through hole 6210 of the substrate 621. It can be understood that the fixing piece 625 should have a certain deformation ability so as to be clamped outside the fixing base 20, so the fixing piece 625 is made of shape memory material, and other parts of the connecting frame 62 can be made of relatively hard materials such as stainless steel, thereby increasing the connection strength. That is, the fixing piece 625 of the connection frame 62 and the bending section 641 connected thereto can be integrally formed by nickel-titanium alloy, and the substrate 621 and the connection piece 623 of the connection frame 62 are integrally formed by stainless steel and then welded or bonded to the fixing piece 625, each bending section 641 is then welded or glued to the gripping section 643 for fixation.

As shown in FIGS. 6-8, the bending section 641 includes a first end 6412 connected to the corresponding fixing piece 625, and a second end 6414 connected to the corresponding gripping section 643, and the bending section 641 is a variable diameter structure, that is, the width of the bending section 641 at the first end 6412 is greater than the width of the bending section 641 at the second end 6414, and the width of the bending section 641 gradually decreases from the first end 6412 to the second end 6414. In this embodiment, the width of the first end 6412 of the bending section 641 is equal to the width of the fixing piece 625, the width of the second end 6414 of the bending section 641 is equal to the width of the gripping section 643, and there is a smooth transition between the first end 6412 and second end 6414 of the bending section 641. Since the valve clamping device 100 often needs to be opened and closed repeatedly during the operation, and the valve leaflets are caught many times, if the rebound stress of the gripping arm 64 is too large, the pulling force of the control line is required to be greater, this will increase the risk of control line breakage. The diameter-reducing structure of the bending section 641 can effectively reduce the stress of the gripping arm 64 in the retracted state, thereby reducing the risk of the control line breaking. In addition, in the prior art, in order to reduce the stress, a hole is opened in the middle of the bending section, but micro-cracks are prone to appear at the opening position, and micro-cracks are often difficult to observe. Under the lower conditions, the micro-cracks near the opening position are prone to fatigue fracture. Therefore, in this embodiment, the stress is reduced through the variable diameter structure, and at the same time, the risk of fatigue fracture caused by the opening is avoided.

Preferably, the width ratio of the second end 6414 of the bending section 641 to the first end 6412 ranges from 0.4 to 0.8; more preferably, the width ratio of the second end 6414 to the first end 6412 of the bending section 641 ranges from 0.5-0.65. If the ratio of the width of the second end 6414 to the first end 6412 is too large, that is, the width of the second end 6414 is too large, the stress of the bending section 641 when the gripping arm 64 is folded is relatively large, and the required pulling force is relatively large, and the risk of breaking the control line is higher; if the ratio of the width of the second end 6414 to the first end 6412 is too small, that is, the width of the second end 6414 is too small, it will affect the clamping force of the gripping arm 64 on the tissue, causing the clamping device 100 to slip off easily.

As shown in FIGS. 5-8, the gripping section 643 of each gripping arm 64 is provided with at least one row of barbs 6433 along its length, and the end of each barb 6433 is rounded to avoid piercing the valve leaflet. Specifically, the gripping section 643 includes a gripping piece 6431 connected to the second end 6414 of the bending section 641, and two row of barbs 6433 connected to both sides of the gripping piece 6431. In this embodiment, the number of barbs 6433 on each side of gripping piece 6431 is four.

There is an angle between each barb 6433 and the clamping piece 6431, and the angle ranges from 30 degrees to 85 degrees, preferably 45 degrees to 65 degrees. If the angle is too large or too small, it will increase the difficulty of capturing the leaflet. The included angle A between each barb 6433 and the gripping piece 6431 may be the same or different. In present embodiment, the included angle A between each barb 6433 and the clamping piece 6431 is 60 degrees.

The effective length of each barb 6433 ranges from 0.3 mm to 2.0 mm, preferably from 0.5 mm to 1.2 mm. The effective lengths of the barbs 6433 may or may not be the same. In present embodiment, the extension lengths of the barbs in each row of barbs 6433 are the same, specifically, the four barbs 6433 at the same row and at the same side of the gripping piece 6431 from the end adjacent to the bending section 641 to the distal end have the effective lengths of L1, L2, L3, and L4 respectively, and L1=L2=L3=L4; in present embodiment, the effective lengths of L1, L2, L3, and L4 are all 0.8 mm.

As shown in FIG. 9, in another embodiment of the tissue gripper 60, the included angle between the barbs in at least one row of barbs 6433 of each gripping section 643 and the corresponding gripping section 643 along the extension direction of the gripping arm increases gradually, and the effective lengths of the barbs 6433 from the end adjacent to the bending section 641 to the distal end also increase gradually. Specifically, the number of barbs 6433 in each row is four, and the included angles between the barbs 6433 and the gripping section 643 from one end adjacent to the bending section 641 to the distal end are A1, A2, A3, A4, and A1≤A2≤A3≤A4, and the effective lengths of the barbs 6433 from the end adjacent to the bending section 641 to the distal end are L1, L2, L3, L4 respectively, and L1≤L2≤L3≤L4. In present embodiment, the angle of A1 is 45 degrees, the angle of A2 is 50 degrees, the angle of A3 is 55 degrees, and the angle of A4 is 60 degrees; the effective length of L1 is 0.4 mm, the effective length of L2 is 0.8 mm, the effective length of L3 is 1.0 mm, and the effective length of the L4 is 1.2 mm. The reason for this setting is that due to the uneven thickness of the leaflet, the edge of the leaflet is the thinnest, and the thickness gradually increases to the junction of the leaflet and the annulus. In accordance with the increased thickness of anatomy structure from the edge to the middle portion of the leaflet, ensure that the force depth of each barb 6433 at different contact positions with the leaflet tissue is roughly the same, ensure the gripping force of the gripping section 643 on the leaflet, and not pierce the leaflet, so that the angle of the barb 6433 is adjusted to adapt to the stress depth of leaflet tissue of different thickness.

As shown in FIG. 8, the width D1 of the gripping section 643 (width D1=the width of the gripping piece 6431+the width of the barbs 6433 on both sides), the width D2 of the second end 6414 of the bending section 641, and the width D3 of the fixing piece 625 have a ratio range (1.5-2):1:(1.5-2), that is, D1:D2:D3=(1.5-2):1:(1.5-2). In this embodiment, the width D1 of the gripping section 643:the width D2 of the second end 6414 of the bending section 641:the width D3 of the fixing piece 625=1.5:1:1.5. If the width D2 is too narrow, the fatigue resistance and tensile strength of the valve clamping device 100 will be reduced; if the width D2 is too wide, the weight of the valve clamping device 100 will increase, this will result that the valve clamping device 100 hung from the leaflet after implantation for a long time, it is not only easy to slip off, but also may strain the target tissue or even cause cardiac dysfunction; and since the tissue gripper 60 is made of shape memory alloy, if D2 is too wide, it will cause the leaflets being by the bending section 641 experience greater stress during heart expansion and contraction movements, resulting in serious tissue damage.

As shown in FIG. 10 and FIG. 11, the distal end of the fixing piece 625 is connected to the connecting frame 62, and the proximal end of the fixing piece 625 is connected to the bending section 641. The fixing piece 625 has a function for fastening and fixing between the tissue gripper 60 and the fixing base 20, this prevents the tissue gripper 60 from being displaced or loosened relative to the fixing base 20 under the unilateral pulling force of the control line, thereby ensuring the reliability of the tissue gripper 60 in the process of capturing the leaflet.

In this embodiment, the fixing piece 625 includes a first fitting portion 6251 and a second fitting portion 6253. The first fitting portion 6251 is to prevent the connection frame 62 from moving up and down after it cooperates with the fixing base 20, that is, it plays the role of proximal and distal limits. The second fitting portion 6253 is to prevent the connection frame 62 from moving left and right after it cooperates with the fixing base 20, that is, it plays the role of left and right limits. The radius of curvature of the proximal portion of the fixing base 20 is greater than the radius of curvature of the fixing piece 625. Specifically, the first fitting portion 6251 is a curved piece corresponding to the first fitting curved surface 212 of the fixing base 20, and the second fitting portion 6523 is a curved piece corresponding to the second fitting curved surface 214 of the fixing base 20, wherein the curvature radius of the first fitting portion 6251 is K3, and the curvature radius of the second fitting portion 6523 is K4. The curvature radius K3 of the first fitting portion 6251 is greater than the curvature radius K1 of the first fitting curved surface 212 of the fixing base 20, and the curvature radius K4 of the second fitting portion 6253 is less than the curvature radius K2 of the second fitting curved surface 212 of the fixing base 20, so that a first avoidance position P1 is reserved between the first fitting curved surface 212 and the first fitting portion 6251, and a second avoidance position P2 is reserved between the second fitting curved surface 214 and the second fitting portion 6523, the contact point between the fixing piece 625 and the fixing frame 21 is just set between the first avoidance position P1 and the second avoidance position P2, so as to prevent the connection between the fixing piece 625 and the fixing base 20 from interfering, thereby ensuring the first fitting portion 6251 stability, that is, to ensure the stability of the proximal and distal limits.

As shown in FIG. 5 and FIG. 6, when the fixing base 20 is accommodated in the connecting frame 62, the two protrusions 23 of the fixing base 20 are snapped into the two slots 6230 of the tissue gripper 60 respectively, so that the fixing base 20 and the tissue gripper 60 are engaged with each other to prevent the tissue gripper 60 from moving back and forth with the fixing base 20, that is, to play the role of front and rear limits.

In order to ensure the safety after implantation, the fixing base 20 and the clamping arm 40 are made of biocompatible metal materials such as stainless steel, cobalt alloy, cobalt-chromium alloy, titanium alloy or nickel-titanium alloy; the actuator assembly 70 is made of biocompatible polymer or metal materials such as polyester, silicone resin, stainless steel, cobalt alloy, cobalt-chromium alloy or titanium alloy. In present embodiment, the fixing base 20, the clamping arm 40 and the actuator assembly 70 are all made of stainless steel.

As shown in FIG. 12, when the actuator assembly 70 actuate the clamping arm 40 to open and close relative to the fixing base 20, the clamping arm 40 can be opened and closed in a greater range relative to the fixing base 20, and the angle between the two clamping arms 40 at most can reach 300 degrees, that is, after the clamp arm 40 is opened relative to the fixing base 20, it can be turned downward to a certain extent, which is beneficial to clamping the leaflet in motion, improving the success rate of clamping, and after clamping, if the effect is found to be unsatisfactory, the valve leaflet can be loosened by turning down the clamping arm 40 and clamped again. In this embodiment, the angle range between the two clamping arms 40 is preferably 0-240 degrees, more preferably 120-180 degrees.

Preferably, an anti-slip structure (not shown) can be provided on the surface of the clamping arm 40 facing the gripping section 643, so as to enhance the friction force when the clamping arm 40 is in contact with the valve leaflet 300, thereby providing a stable clamping force, and being able to avoid damage to the valve leaflet 300 by the clamping arm 40. The anti-slip structure may be a protrusion or a groove disposed on the inner surface of the receiving groove 45 of the clamping frame 44, or a gasket made of a biocompatible material with a higher friction coefficient attached to the inner surface of the receiving groove 45.

Preferably, an active drug can also be applied on the inner surface of the receiving groove 45 of the clamping arm 40 and/or on each gripping section 643, so as to promote the endothelial cell crawling and grow of the leaflet tissue on the inner surface of the clamping arm 40 and on the gripping arm 64.

It should be noted that the two gripping sections 643 of the tissue gripper 60 are also respectively provided with control lines, and the gripping sections 643 can be pulled up to the central axis of the valve clamping device 100 by pulling or loosening the control lines, so as to facilitate delivery; or allow the gripping arm 64 to rebound and return to its natural state due to its own elastic memory performance by releasing the gripping section 643. The gripping section 643 unfolds relative to the fixing base 20 to press the leaflet 300 to the clamping arm 40 to clamp the leaflet 300. Specifically, the control line may be a metal wire made of nickel-titanium alloy, etc., and since it has nothing to do with the improvement and creation of the present application, details will not be described here.

The following takes the mitral valve repair process as an example to illustrate the operation method of the valve clamping device of the present application, which mainly includes the following steps:

Step 1: detachably connect the valve clamping device 100 to the distal end of the delivery device, and tighten the control line toward the proximal end to control the gripping arm 64 to be closed relative to the fixing base 20, so that the gripping section 643 of the gripping arm 64 is close to fit on the surface of the fixing base 20. Then move the actuator shaft 72 to the proximal end to allow the connecting rod 76 to actuate the clamping arm 40 to close relative to the fixing base 20, so that the valve clamping device 100 is in a fully folded state, and the tissue gripper 60 and the clamping arm 40 are all close to the fixing base 20, keep the folded state unchanged.

Step 2: after femoral vein puncture and transseptal puncture, advancing the distal end of the delivery device and the valve clamping device 100 from the left atrium to pass through the mitral valve into the left ventricle using the adjustable sheath.

Step 3: adjust the relative position of the valve clamping device 100 and the mitral valve, so that the valve clamping device 100 is close to the anterior leaflet and the posterior leaflet of the mitral valve.

Step 4: move the actuator shaft 72 toward the distal end, thereby actuate the connecting rod 76 to actuate the clamping arm 40 to open relative to the fixing base 20.

Step 5: retract the valve clamping device 100 toward the proximal end, so that the clamping arm 40 holds the valve leaflet in the left ventricular side.

Step 6: release the control of each control line to the corresponding gripping arm 64 to release the gripping arms 64 on both sides. The gripping arm 64 on each side presses the valve leaflet 300 in the atrium side and cooperate with the clamping arm 40 to hold the leaflets (as shown in FIG. 13).

Step 7: move the actuator shaft 72 toward the proximal end, and the actuator shaft 72 actuate the connecting rod to actuate the clamping arm 40 to close relative to the fixing base 20 until the valve clamping device 100 is completely closed.

Step 8: release the connection between the valve clamping device 100 and the delivery device and the control lines, and withdraw the delivery device and the control lines from the patient's body, at this time, the valve clamping device 100 pulls the anterior and posterior leaflets of the mitral valve towards each other, a double-orifice mitral valve is obtained, the edge-to-edge repair of the mitral valve is completed, and the valve clamping device 100 is indwelling in the patient.

Please refer to FIG. 14 and FIG. 15, the structure of the valve clamping device 100*a* provided by the second embodiment of the present application is similar to the structure of the valve clamping device 100 in the first embodiment, the difference is that in the second embodiment, the structure of the gripping arm 64*a* is slightly different from that of the gripping arm 64 in the first embodiment. Specifically, a bending portion 645 is provided between the gripping section 643 of each gripping arm 64*a* and the corresponding bending section 641, and the bending portion 645 is bent toward the side away from the connecting frame 62, so that the gripping section 643 of the gripping arm 64 is approximately parallel to the clamping frame 44 of the clamping arm 40 in a natural state. Therefore, when the gripping arm 64*a* captures the leaflet, the gap between the barb 6433 and the clamping frame 44 of the clamping arm 40 is relatively uniform, and the barb 6433 can contact the leaflet 300 synchronously, so as to improve the success rate and stability of capturing the leaflet 300.

Perform performance tests on tissue gripper and fatigue tests on valve clamping devices.

Tissue Grip Performance Test

Three groups of clamping arms were made by using the same nickel-titanium alloy material and manufacturing process respectively, wherein the first group was the tissue gripper (variable diameter structure with a reduced width of embodiments A1-A4 in FIG. 16) adopted by the present application; the second group was the tissue gripper with constant dimension (constant diameter structure with an equal width) in the prior art (constant diameter structure with an equal width of the comparative example B1-B4 in FIG. 16); and the third group is the tissue gripper in the prior art with equal width and with openings formed by laser cutting on the gripper (the equal-width structure with openings of comparative examples C1-C4 in FIG. 16), the following performance tests were performed on several groups of tissue gripper, and the test results are shown in FIG. 16 shown.

1. Tissue Gripper Fatigue Test

To test the fatigue resistance of the tissue gripper itself, the test equipment is the AWT-1000 artificial heart valve fatigue testing machine of Shanghai Heart partner Testing Equipment Co., Ltd. It is tested whether the tissue gripper is broken or cracked due to load during the fatigue test cycle, and the test results are shown in FIG. 16.

Fatigue test parameters are as follows: cyclic pulling force (peak value): 0.80N±0.30N, amplitude: 1 mm, frequency: 50 Hz, water bath temperature: 37° C.±0.5° C., cycle: ≥400 million times.

2. Test the Retraction Force of the Control Line on the Tissue Gripper

The retracting force of the same control lines on the three groups of tissue grippers was tested. The test equipment is HY-0580 electronic universal tensile testing machine produced by Shanghai Hengyi Precision Instrument Co., Ltd. The test method is as follows: connect the valve clamping device with a simple handle, use two U-shaped control lines to pass through the control holes at the two free ends of each gripping arm, and the control lines pass through the proximal end of the simple handle, fix the simple handle on the machine table of the tensile testing machine, hook the moving end of the tensile testing machine to the proximal end of the control line, move the moving end at a constant speed of 4.5 mm/min, and record the pulling force value when the tissue gripper has the gripping sections on both sides closed to a substantially parallel state, the test result is shown in FIG. 16.

3. Control Line Fatigue Performance Test

Test the fatigue resistance of control lines of three groups of tissue grippers. The test equipment is HY-0580 electronic universal tensile testing machine produced by Shanghai Hengyi Precision Instrument Co., Ltd. The test method is as follows: connect the valve clamping device with a simple handle, use two U-shaped control lines to pass through the control holes at the two free ends of each clamping arm, and the control lines pass through the proximal end of the simple handle, fix the simple handle on the platform of the tensile testing machine, hook the moving end of the tensile testing machine to the proximal end of the control line, repeat the action of the tissue gripper being retracted and released under the control of the control line, and the number of tests is 50 times. Observe the control line after the test, if any of scratches, abrasions, cracks, or breaks occurs, it is judged to have failed the test, the test results are shown in FIG. 16.

From the test results shown in FIG. 16, it can be seen that:

1). This application can effectively reduce the retraction force required to control the tissue gripper by setting a variable diameter structure on the tissue gripper, which can not only ensure the fatigue resistance of the control line, but also ensure the tissue gripper itself fatigue resistance;

2). The tissue grippers in the prior art are not provided with a diameter-reducing structure, and the pulling force required to control the retraction of the tissue grippers is obviously larger. Although the fatigue resistance of the tissue gripper itself can be guaranteed, the control line cannot be guaranteed. fatigue resistance;

3). The tissue clamps having openings in the prior art, although the pulling force required to control the retraction of the tissue gripper can be reduced and the fatigue resistance of the control line can be ensured, the fatigue resistance of the tissue gripper itself cannot be guaranteed.

In summary, compared with the prior art, the tissue gripper of the present application has better fatigue resistance, requires less pulling force and retracting force, and has a lower risk of breakage of the control line.

Valve Clamping Device Fatigue Test

Whether the valve clamping device adopting the tissue gripper of the present application can meet the 10-year load as an implantable medical device after clamping the two leaflets of the mitral valve is verified by a fatigue test. Before the test, fix the artificial mitral valve model with the valve clamping device to simulate the effect of edge-to-edge repairing, and then place the mitral valve model with the valve clamping device in a fatigue testing machine that simulates the beating of the left heart system of the human heart, conduct non-destructive fatigue tests, and record the sliding of the valve clamping device due to the load and the damage to the leaflets during the fatigue test period.

Test equipment: AWT-1000 artificial heart valve fatigue testing machine of Shanghai Heart partner Testing Equipment Co., Ltd.

Test standard: test according to the method of "fatigue test" in ISO 5840 and GB12279-2008 "cardiovascular implant artificial heart valve", cycle: ≥400 million times, the test result is that the valve clamping device of this embodiment meets the requirements of relevant requirements, the valve clamping device did not slip during the test period, and the valve clamping device did not cause damage to the valve leaflets.

It should be noted that, the above content is described by taking the valve clamping device as an example to reduce or treat "mitral regurgitation". It can be understood that, in other embodiments, the valve clamping device can also be used to reduce or treat "tricuspid regurgitation", and its principle and structure are the same as those used in the embodiment of this application to solve "mitral regurgitation" The principle and structure of the valve clamping device are roughly the same. It only needs to form a plurality of clamps through multiple sets of proximal clips and distal clips, and each clamp can clamp a valve leaflet separately, so I won't repeat them here.

It should be noted that, on the premise of not departing from the principles of the embodiments of the present application, the specific technical solutions in the above embodiments can be applied to each other, and will not be repeated here.

The above is the implementation of the embodiment of the present application. It should be pointed out that for those of ordinary skill in the art, without departing from the principle of the embodiment of the present application, some improvements and modifications can also be made. These improvements and modifications are also It is regarded as the scope of protection of this application.

What is claimed is:

1. A tissue gripper, comprising:

a connection frame, the connection frame comprising two connection pieces spaced apart and opposite to each other;

two gripping arms, the two gripping arms respectively arranged on sides of the connection pieces, each of the gripping arms extending away from the other one of the gripping arms, and each of the gripping arms comprising a bending section connected to the corresponding connection piece, and a gripping section connected to the bending section and extending away from the corresponding connection piece, a width of the bending section being less than a width of the gripping section, and less than a width of the corresponding connection piece;

wherein each of the connection pieces is connected to the corresponding bending section through a bent fixing piece, the fixing piece on the corresponding connection piece bending toward the other one of the connection pieces, and each of the bending sections bending away from the other one of the bending sections;

wherein each of the bending sections includes a first end connected to the corresponding fixing piece, and a second end connected to the corresponding gripping section, a width of the bending section at the first end is greater than a width of the bending section at the second end;

wherein the width of the bending section gradually decreases from the first end to the second end.

2. The tissue gripper according to claim 1, wherein the width of the first end of the bending section is equal to the width of the fixing piece, the width of the second end of the bending section is equal to the width of the gripping section, and the bending section has a smooth transition from the first end to the second end.

3. The tissue gripper according to claim 1, wherein the gripping section of each of the gripping arms is provided with at least one row of barbs along a length direction thereof.

4. The tissue gripper according to claim 3, wherein an end of each of the at least one row of barbs is rounded.

5. The tissue gripper according to claim 3, wherein extension lengths of the barbs in the at least one row of barbs gradually increase along an extension direction of the gripping arm.

6. The tissue gripper according to claim 3, wherein included angles between the barbs in the at least one row of barbs and the corresponding gripping section gradually increases along an extending direction of the respective gripping arm.

7. The tissue gripper according to claim 1, wherein a bending portion is provided between the gripping section and the corresponding bending section of each of the gripping arms, and the bending portion is bent toward a side away from the connection frame.

8. The tissue gripper according to claim 1, wherein the tissue gripper is at least partially made of shape memory material, and the tissue gripper has a natural unfolded state and a folded state.

9. The tissue gripper according to claim 8, wherein the bending section is made of shape memory material, and an angle between the gripping sections of the two gripping arms is greater than 180 degrees in the natural state of the tissue gripper.

10. A valve clamping device, comprising:
a fixing base;
a pair of clamping arms, wherein the pair of clamping arms are configured to open and close relative to the fixing base; and
a tissue gripper according to claim 1, the tissue gripper being arranged between the fixing base and the pair of clamping arms, each of the gripping arms of the tissue gripper is configured to cooperate with one of the pair of clamping arms to clamp a leaflet.

11. The valve clamping device according to claim 10, wherein the fixing base is accommodated in the connection frame, at least one of the connection pieces of the connection frame is provided with a slot, and the fixing base is provided with a protrusion engaged in the slot.

12. The valve clamping device according to claim 11, wherein a curvature radius of a proximal portion of the fixing base is greater than a curvature radius of the fixing piece.

* * * * *